United States Patent
Frenkel et al.

(10) Patent No.: US 6,696,600 B2
(45) Date of Patent: Feb. 24, 2004

(54) L-DOPA ETHYL ESTER SALTS AND USES THEREOF

(75) Inventors: Anton Frenkel, Modiin (IL); Ramy Lidor-Hadas, Kfar Saba (IL)

(73) Assignee: Teva Pharmaceutical Industries, Ltd., Petach-Tikva (IL)

(*) Notice: Subject to any disclaimer, the term of this patent is extended or adjusted under 35 U.S.C. 154(b) by 0 days.

(21) Appl. No.: 10/292,028

(22) Filed: Nov. 12, 2002

(65) Prior Publication Data

US 2003/0162832 A1 Aug. 28, 2003

Related U.S. Application Data

(60) Provisional application No. 60/350,477, filed on Nov. 13, 2001.

(51) Int. Cl.$^7$ .............................................. C07C 229/00

(52) U.S. Cl. ..................... 560/445; 560/42; 514/538; 514/567; 514/649

(58) Field of Search ................... 560/445, 42; 514/538, 514/567, 649

(56) References Cited

U.S. PATENT DOCUMENTS

| | | | |
|---|---|---|---|
| 3,803,120 A | | 4/1974 | Felix |
| 3,883,674 A | | 5/1975 | Ninagawa et al. |
| 4,873,263 A | | 10/1989 | Repta |
| 5,354,885 A | * | 10/1994 | Milman et al. ............... 560/43 |
| 5,525,631 A | * | 6/1996 | Milman et al. ............. 514/567 |
| 5,607,969 A | | 3/1997 | Milman et al. |
| 5,639,913 A | | 6/1997 | Lidor et al. |
| 5,738,874 A | | 4/1998 | Conte et al. |
| 5,780,057 A | | 7/1998 | Conte et al. |
| 5,840,756 A | | 11/1998 | Cohen et al. |
| 6,183,778 B1 | | 2/2001 | Conte et al. |
| 6,218,566 B1 | * | 4/2001 | Lidor et al. .................... 560/42 |
| 6,238,699 B1 | | 5/2001 | Rubin |
| 6,294,200 B1 | | 9/2001 | Conte et al. |
| 6,376,545 B1 | | 4/2002 | Levin |
| 6,514,938 B1 | | 2/2003 | Gad et al. |
| 2002/0151589 A1 | | 10/2002 | Levin et al. |
| 2003/0135065 A1 | | 7/2003 | Lidor-Hadas et al. |

FOREIGN PATENT DOCUMENTS

| | | |
|---|---|---|
| GB | 1342286 | 1/1974 |
| GB | 1364505 | 8/1974 |
| WO | 9917745 | 4/1999 |
| WO | 0027385 | 5/2000 |

OTHER PUBLICATIONS

U.S. patent application Ser. No. 10,194,507, Licht et al., filed Jul. 12, 2002.
U.S. patent application Ser. No. 10,195,036, Licht et al., filed Jul. 12, 2002.
U.S. patent application Ser. No. 10,301,540, Hayardeny-Nisimov et al., filed Nov. 21, 2002.
Aarli, J.A., Gilhus, N.E., Neurology 39 (suppl.2):82–85 (Exhibit 26).
Bastin et al., "Salt Selection and Optimisation Procedures for Pharmaceutical New Chemical Entities" Organic Process Research and Development, 2000(4): 427–435 (Exhibit 27).
Cedarbaum et al., Neurology 40:995–997 (1990) (Exhibit 28).
Cooper et al., "L–Methyl Ester Dopa–A Candidate for Chronic Systemic Delivery of L–Dopa in Parkinson's Disease" Clinical Neuropharmacol. 7(1):88–98 (1984) (Exhibit 29).
"Excipients: Microcrystalline Cellulose," Pformulate (2000) (Exhibit 30).
"Excipients: Starch 1500: Partially Pregelatinized Maize Starch," Colorcon (2001) (Exhibit 31).
FDA Guidance for Industry SUPAC–MR: Modified Release Oral Dosage Forms CDER, Sep. 1997 (Exhibit 32).
Fix et al., Pharmaceutical Research 6 (6):501–505 (1989) (Exhibit 33).
"Formulating for Controlled Release with Methocel Premium cellulose ethers," Dow, The Dow Chemical Company (1995) (Exhibit 34).
Friedman and Lannon, Clinical Neuropharm. 12:220–223 (1989) (Exhibit 35).
Ginsburg et al., Zh. Obshch. Khim. 39:1168–1170 (1969) (Exhibit 36).
Goetz et al., Neurology 37:875–878 (1987) (Exhibit 37).
Kaolin for Rubber and Chemical Industry, "Kaolin" AD (Exhibit 38).
"Klucel hydroxypropylcellulose," Aqualon, Hercules Inc. (2000) (Exhibit 39).
Kurlan, R., et al., Ann. Neurol. 20:262–265 (1986) (Exhibit 40).

(List continued on next page.)

*Primary Examiner*—Alan L. Rotman
*Assistant Examiner*—Hector M. Reyes
(74) *Attorney, Agent, or Firm*—John P. White; Cooper & Dunham LLP

(57) ABSTRACT

The present invention provides non-hygroscopic, crystalline salts of levodopa ethyl ester (LDEE), wherein the salt is the octanoate salt, the myristate salt, the succinate salt, the succinate dihydrate salt, the fumarate salt or the fumarate dihydrate salt of levodopa ethyl ester. The subject invention also encompasses compositions comprising a levodopa ethyl ester salt and a carrier and processes for making these compositions. In addition, the subject invention concerns pharmaceutical compositions comprising a levodopa ethyl ester salt and a pharmaceutically acceptable carrier, as well as processes for making these pharmaceutical compositions. Furthermore, the subject invention includes methods of treating a subject afflicted with Parkinson's disease, senile dementia, dementia of the Alzheimer's type, a memory disorder, depression, hyperactive syndrome, an affective illness, a neurodegenerative disease, a neurotoxic injury, brain ischemia, a head trauma injury, a spinal trauma injury, schizophrenia, an attention deficit disorder, multiple sclerosis and seizures by the administration of levodopa ethyl ester salts.

20 Claims, No Drawings

OTHER PUBLICATIONS

Kurth, M.C., et al. Neurology 43:1036–1039 (1993) (Exhibit 41).

Marrel et al., Eur. J.Med.Chem.—Chim.Ther., 1985, 20(5):459–465 (Exhibit 42).

Morris et al., "An Integrated Approach to the Selection of Optimal Salt Form for a New Drug Candidate" Int'l. J. Pharmaceut., 1994, 105: 209–217 (Exhibit 43).

Pahwa et al., Neurology 43:677–681 (1993) (Exhibit 44).

Rodnitzki, R.L. et al., Neurology 39(suppl.2) 92–95 (1989) (Exhibit 45).

Rondot et al., Neurology 39 (suppl.2): 74–77 (1989) (Exhibit 46).

Ross, Malcolm S.F., and Rasis, Mina, "Pharmacopeia Forum: Mega Paddle—A Recommendation to Modify Apparatus 2 Used in the USP General Test for Dissolution," *Drug Standards*, 24(3) (May–Jun. 1998) (Exhibit 47).

"Salt selection, reducing time to market". SSCI App. Notes, 1999(4): 1–4 (Exhibit 48).

"Sinemet CR (Carbidopa–Levodopa) Sustained Release Tablets," Merck & Co./Bristol–Myers Squibb Co., 1996, available at http://www.sinemetcr.com/cross site/CurrentSinemetCRPI.pdf (Exhibit 49).

Stocchi, F., et al., Movement Disorders, 7:249–256 (1992) (Exhibit 50).

Streng, "Physical Chemical Characterization of Drug Substances" Drug Discovery Today, 1997, 2(10): 415–426 (Exhibit 51).

"Syloid & Sylox Silicas for the Pharmaceutical and Personal Care Markets," Grace Davison Products, W.R. Grace & Co. (1999) (Exhibit 52).

Venter et al., S. Afr. Tydskr. Chem. 31:135–137 (1978) (Exhibit 53).

* cited by examiner

L-DOPA ETHYL ESTER SALTS AND USES THEREOF

This application claims benefit of U.S. Provisional Application No. 60/350,477, filed Nov. 13, 2001, the contents of which are hereby incorporated by reference.

Throughout this application, various references are cited, using arabic numbers within parentheses. Full citations for these references can be found at the end of the specification, immediately preceding the claims. These publications, in their entireties, are hereby incorporated by reference into the application to more fully describe the state of the art to which the invention pertains.

FIELD OF THE INVENTION

The present invention concerns the use of levodopa ethyl ester (LDEE) salts to treat Parkinson's disease, senile dementia, dementia of the Alzheimer's type, a memory disorder, depression, hyperactive syndrome, an affective illness, a neurodegenerative disease, a neurotoxic injury, brain ischemia, a head trauma injury, a spinal trauma injury, schizophrenia, an attention deficit disorder, multiple sclerosis, withdrawal symptoms, epilepsy, convulsions or seizures.

BACKGROUND OF THE INVENTION

Typically, Parkinsonian patients are routinely treated with a combination of levodopa (L-DOPA) and an L-DOPA decarboxylase inhibitor such as carbidopa or benserazide. Unfortunately, after an initial period of satisfactory, smooth and stable clinical benefit from L-DOPA therapy lasting on the average 2–5 years, the condition of many patients deteriorates and they develop complex dose-related as well as unpredictable response fluctuations. The causes of the response fluctuations are probably multiple and complex, but pharmacokinetics problems (primarily faulty absorption of L-DOPA) may play a critical role. There is a correlation between the clinical fluctuations and the oscillations of L-DOPA plasma levels. Many of the problems are a result of the unfavorable pharmacokinetics properties of L-DOPA, i.e. very poor solubility, poor bio-availability and short half-life in vivo.

A typical problem commonly seen with these patients is the "on-off" oscillations in which daily motor activity is dominated by remarkable swings between off hours, when they are severely incapacitated, rigid, unable to move, and sometimes to speak or swallow, to on periods where they are responsive to L-DOPA and can, more or less, perform. The current treatments (apomorphine, lisuride) used to treat patients in the off period are unsatisfactory.

L-DOPA ethyl ester free base (LDEE) [10], a drug substance in phase III clinical trials for the treatment of Parkinson's disease, is a white, flowable, non-hygroscopic, crystalline powder with melting point of 87.1–87.5° C. It is stable at low temperature and low humidity, soluble in water (52 mg/ml), and its aqueous solution pH is 8.2. LDEE is more soluble than L-DOPA.

The properties of LDEE free base may, however, cause difficulties in pharmaceutical production such as the need for special conditions of storage. Processing of the pharmaceutical raw material has to be fast and performed at low temperature and low air humidity.

Thus, there is a need for a form of LDEE in addition to the free base, such as salts of LDEE. An advantage of a salt of LDEE over LDEE free base is that a salt has higher solubility and therefore usually provides better bioavailability of drug. High solubility is also important for preparation of injection dosage form; injection of LDEE as a salt may be an effective rescue therapy for patients with Parkinson's disease. Salts of LDEE may also provide a better stability profile than the free base.

However, salts are sometimes hygroscopic, therefore pharmaceutical solid form preparation may be very difficult. For instance, absorption of atmospheric humidity usually causes physical and chemical transformation of the drug product. L-DOPA ethyl ester itself is unstable in the presence of water due to hydrolysis to L-DOPA and ethanol. In the pharmaceutical industry, materials with hygroscopic point below 80% (j<80% RH) tend to be problematic and need special storage and processing techniques such as dry rooms and microencapsulation of the drug substance.

The only known salt of LDEE is the hydrochloride salt. The hydrochloride salt of LDEE is extremely hygroscopic [1,2]. The possibility of pharmaceutically acceptable acid salts of LDEE as candidates for pharmaceutical use (for a rectally absorbable form [3] and in the treatment of Alopecia [4]), have also been mentioned, but no example of practical preparation of such salts has ever been disclosed.

In addition, no quantitative data on LDEE salts, hygroscopicity, nor hygroscopic points have ever been measured. Conclusions about hygroscopicity have only been based on qualitative observations of solid materials exposed to atmosphere.

SUMMARY OF THE INVENTION

The subject invention provides a non-hygroscopic, crystalline salt of levodopa ethyl ester (LDEE), wherein the salt is the octanoate salt, the myristate salt, the succinate salt, the succinate dihydrate salt, the fumarate salt or the fumarate dihydrate salt of levodopa ethyl ester.

In addition, the subject invention encompasses a process for producing a salt of levodopa ethyl ester, which comprises:

(a) reacting levodopa ethyl ester with an acid, wherein the acid is octanoic acid, myristic acid, succinic acid or fumaric acid, so as to form a solution; and (b) recovering the salt so formed to produce a salt of levodopa ethyl ester.

DETAILED DESCRIPTION OF THE INVENTION

The subject invention provides a non-hygroscopic, crystalline salt of levodopa ethyl ester (LDEE), wherein the salt is the octanoate salt, the myristate salt, the succinate salt, the succinate dihydrate salt, the fumarate salt or the fumarate dihydrate salt of levodopa ethyl ester.

In one embodiment, the salt is the octanoate salt of levodopa ethyl ester.

In another embodiment, the salt is the myristate salt of levodopa ethyl ester.

In an additional embodiment, the salt is the succinate salt of levodopa ethyl ester.

In a further embodiment, the salt is the succinate dihydrate salt of levodopa ethyl ester.

In yet another embodiment, the salt is the fumarate salt of levodopa ethyl ester.

In an added embodiment, the salt is the fumarate dihydrate salt of levodopa ethyl ester.

The subject invention further provides a composition comprising the salt of levodopa ethyl ester and a carrier.

The subject invention also provides a pharmaceutical composition comprising the salt of levodopa ethyl ester (LDEE) in an amount sufficient to produce a therapeutically effective amount of levodopa (L-DOPA) and a pharmaceutically acceptable carrier.

Additionally, the subject invention provides a method for treating a subject suffering from a disease, wherein the disease is Parkinson's disease, senile dementia, dementia of the Alzheimer's type, a memory disorder, depression, hyperactive syndrome, an affective illness, a neurodegenerative disease, a neurotoxic injury, brain ischemia, a head trauma injury, a spinal trauma injury, schizophrenia, an attention deficit disorder, multiple sclerosis, withdrawal symptoms, epilepsy, convulsions or seizures comprising administering to the subject the non-hygroscopic, crystalline salt of levodopa ethyl ester (LDEE) in an amount sufficient to produce an amount of levodopa (L-DOPA) effective to treat the disease.

In one embodiment, the disease is Parkinson's disease.

In another embodiment, the amount of the salt of levodopa ethyl ester (LDEE) sufficient to produce a an amount of levodopa (L-DOPA) effective to treat the disease is an amount from 100 mg to 600 mg.

In a further embodiment, the amount of the salt of levodopa ethyl ester sufficient to produce a an amount of levodopa effective to treat the disease is an amount from 150 mg to 550 mg.

In an added embodiment, the amount of the salt of levodopa ethyl ester sufficient to produce a an amount of levodopa effective to treat the disease is an amount from 200 mg to 500 mg.

In still another embodiment, the amount of the salt of levodopa ethyl ester sufficient to produce a an amount of levodopa effective to treat the disease is an amount from 250 mg to 450 mg.

In one embodiment, the amount of the salt of levodopa ethyl ester sufficient to produce a an amount of levodopa effective to treat the disease is an amount from 300 mg to 400 mg.

In a further embodiment, the amount of the salt of levodopa ethyl ester sufficient to produce a an amount of levodopa effective to treat the disease is about 350 mg.

In an additional embodiment, the administration is oral, buccal, topical, nasal, subcutaneous, rectal, intravenous, intradermal, or intraperitoneal administration.

In another embodiment, the administration is oral.

In one embodiment, the subject is human.

The subject invention also provides a method of providing increased plasma levels of levodopa (L-DOPA) in a subject in need of increased plasma levels of levodopa (L-DOPA) comprising administering to the subject the pharmaceutical composition.

In an added embodiment of the use, the subject is human.

The subject invention further provides the use of the salt of levodopa ethyl ester (LDEE) for the manufacture of a medicament for the treatment of a disease, wherein the disease is Parkinson's disease, senile dementia, dementia of the Alzheimer's type, a memory disorder, depression, hyperactive syndrome, an affective illness, a neurodegenerative disease, a neurotoxic injury, brain ischemia, a head trauma injury, a spinal trauma injury, schizophrenia, an attention deficit disorder, multiple sclerosis, withdrawal symptoms, epilepsy, convulsions or seizures in a subject, wherein the salt of levodopa ethyl ester is present in an amount sufficient to produce a therapeutically effective amount of levodopa (L-DOPA).

In one embodiment of the use, the disease is Parkinson's disease.

The subject invention also provides the use of the salt of levodopa ethyl ester (LDEE) for the manufacture of a medicament to provide increased plasma levels of levodopa (L-DOPA) in a subject in need of increased plasma levels of levodopa (L-DOPA), wherein the salt of levodopa ethyl ester is present in an amount sufficient to produce an amount of levodopa (L-DOPA) effective to treat the disease.

In another embodiment of the use, the amount of the salt of levodopa ethyl ester (LDEE) sufficient to produce an amount of levodopa (L-DOPA) effective to treat the disease is an amount from 100 mg to 600 mg.

In a further embodiment of the use, the amount of the salt of levodopa ethyl ester sufficient to produce an amount of levodopa effective to treat the disease is an amount from 150 mg to 550 mg.

In an added embodiment of the use, the amount of the salt of levodopa ethyl ester sufficient to produce an amount of levodopa effective to treat the disease is an amount from 200 mg to 500 mg.

In still another embodiment of the use, the amount of the salt of levodopa ethyl ester sufficient to produce an amount of levodopa effective to treat the disease is an amount from 250 mg to 450 mg.

In one embodiment of the use, the amount of the salt of levodopa ethyl ester sufficient to produce an amount of levodopa effective to treat the disease is an amount from 300 mg to 400 mg.

In a further embodiment of the use, the amount of the salt of levodopa ethyl ester sufficient to produce an amount of levodopa effective to treat the disease is about 350 mg.

In an additional embodiment of the use, the medicament is formulated for oral, buccal, topical, nasal, subcutaneous, rectal, intravenous, intradermal, or intraperitoneal administration.

In another embodiment of the use, the medicament is formulated for oral administration.

In still another embodiment of the use, the subject is human.

The subject invention further provides the pharmaceutical composition for the treatment of a disease, wherein the disease is Parkinson's disease, senile dementia, dementia of the Alzheimer's type, a memory disorder, depression, hyperactive syndrome, an affective illness, a neurodegenerative disease, a neurotoxic injury, brain ischemia, a head trauma injury, a spinal trauma injury, schizophrenia, an attention deficit disorder, multiple sclerosis, withdrawal symptoms, epilepsy, convulsions or seizures in a subject, wherein the salt of levodopa ethyl ester is present in an amount sufficient to produce a therapeutically effective amount of levodopa (L-DOPA).

In one embodiment of the pharmaceutical composition, the disease is Parkinson's disease.

The subject invention also provides the pharmaceutical composition for the provision of increased plasma levels of levodopa (L-DOPA) in a subject in need of increased plasma levels of levodopa (L-DOPA), wherein the salt of levodopa ehtyl ester is present in an amount sufficient to produce an amount of levodopa (L-DOPA) effective to treat the disease.

In another embodiment of the pharmaceutical composition, the amount of the salt of levodopa ethyl ester (LDEE) is an amount from 100 mg to 600 mg.

In a further embodiment of the pharmaceutical composition, the amount of salt of levodopa ethyl ester is an amount from 150 mg to 550 mg.

In an added embodiment of the pharmaceutical composition, the amount of salt of levodopa ethyl ester is an amount from 200 mg to 500 mg.

In still another embodiment of the pharmaceutical composition, the amount of salt of levodopa ethyl ester is an amount from 250 mg to 450 mg.

In one embodiment of the pharmaceutical composition, the amount of salt of levodopa ethyl ester is an amount from 300 mg to 400 mg.

In a further embodiment of the pharmaceutical composition, the amount of salt of levodopa ethyl ester is about 350 mg.

In an additional embodiment, the pharmaceutical composition is formulated for oral, buccal, topical, nasal, subcutaneous, rectal, intravenous, intradermal, or intraperitoneal administration.

In another embodiment, the pharmaceutical composition is formulated for oral administration.

In still another embodiment of the pharmaceutical composition, the subject is human.

The subject invention further provides a process for producing a salt of levodopa ethyl ester, which comprises:

(a) reacting levodopa ethyl ester with an acid, wherein the acid is octanoic acid, myristic acid, succinic acid or fumaric acid, so-as to form a salt solution; and (b) recovering the salt so formed thereby producing the salt of levodopa ethyl ester.

In addition, the subject invention provides a process for producing the composition comprising admixing the salt of levodopa ethyl ester, and a carrier.

The subject invention also provides a process for producing the pharmaceutical composition comprising admixing the salt of levodopa ethyl ester, and a pharmaceutically acceptable carrier.

As used herein, a non-hygroscopic compound is defined as a compound that absorbs less than 1% water at 80% relative humidity (RH) for 24 hrs [11].

This invention will be better understood from the Experimental Details which follow. However, one skilled in the art will readily appreciate that the specific methods and results discussed are merely illustrative of the invention as described more fully in the claims which follow thereafter.

EXPERIMENTAL EXAMPLES

Hygroscopicity of LDEE Salts Study

There are many methods of quantitative evaluation of hygroscopicity of solid products without measuring the hygroscopic point. The most widely used method is based on measuring the weight gain of a solid sample in a humidity chamber. Products that at relative humidity of 80% (RH=80%) demonstrate low water absorption ability (lower than 1% during 24 hrs) have hygroscopic point below 80% and are not hygroscopic at normal conditions.

This method was used for screening the hygroscopicity of several LDEE salts. It also provides a comparison of the hygroscopic properties of different solids by comparison of water absorption rates under the same conditions.

In the present study a sample of solid material (1–4 g) in an open crucible was incubated in a closed dessicator with constant humidity (RH=80%, T=20±2° C.). The weight of the samples was measured every 2–3 hrs during 12–24 hrs.

Several salts of LDEE were prepared. Unexpectedly, four salts were found to be non-hygroscopic: Succinate dihydrate (Examples 23 and 24), Octanoate (Example 19), Myristate (Example 27) and Fumarate Dihydrate (Example 25).

Preparation of L-DOPA Ethyl Ester Salts

Preparation and selection of salts that have different physical properties are detailed in the literature [5,6,7]. It is accepted that the most stable crystalline salts are formed if there is a difference of more than 3 units of $pK_a$ between the organic base and the counterion ($DpK_a>3$) [6]. $PK_a$ of LDEE free base is known to be 7.24 [8]. Thus, LDEE salts with acids having $pK_a>4.2$ will be unstable. This fact is illustrated in Example 1 below, in which the crystallization of LDEE palmitate was attempted. After dissolution of LDEE base and palmitic acid in absolute alcohol, the solution was cooled, and instead of forming a new salt, pure palmitic acid was crystallized out, and no solid crystalline salt was formed. This was reasonable since palmitic acid has a $pK_a=4.8$ and $DpK_a=2.4$.

The hygroscopic salts could not be precipitated from the reaction mixture in which they were prepared, the only way to prepare them was to evaporate the solvent to dryness. All salts (except succinate dihydrate, Example 24 and fumarate dihydrate, Example 25) reported in the examples (Examples 2–8, 10–12, 14,15, 17–23 and 26–28) were prepared by solvent evaporation from the salt solution as follows: LDEE (obtainable following the procedures of references 1, 2 or 9, which are hereby incorporated by reference) was reacted with the acid in ethanolic solution, the alcohol was then evaporated from the reaction solution, a non-polar solvent (toluene or chloroform) was added to the residue and evaporated. This procedure (solvent exchange) was repeated 2–3 times in order to remove all ethanol from the reaction mixture.

All the salts (except succinate dihydrate and fumarate dihydrate) prepared by this procedure could not be solidified in the presence of polar solvents as water or ethanol. Thus, a complete removal of these solvents is necessary.

Since the palmitate salt could not be crystallized as described in Example 1, it was prepared by solvent evaporation as described in Example 20.

Precipitation of LDEE Salts

In order to purify the newly prepared solid salts, reprecipitation was employed. Since the ethanol and water mixture was not suitable, less polar solvents were used. The salts were precipitated by either cooling or by partial evaporation of the solvent. Thus LDEE benzoate was precipitated from chloroform-hexane (Example 9), LDEE citrate was precipitated from IPA/Ethylacetate (Example 13), LDEE S(+) mandelate was prepared by evaporative precipitation from chloroform (Example 16).

Example 1

Attempted Crystallization of LDEE Palmitate 10.0 g dry LDEE were suspended in 50 ml absolute alcohol and 11.38 g solid Palmitic acid (1 equivalent) were added while stirring. The suspension was heated and at 34° C., a complete dissolution of the solids was observed. The reaction mixture was cooled and white crystalline solids were precipitated. The solids were filtered and dried under vacuum at 40° C. 7.4 g of pure Palmitic acid (plate crystals, m.p. 61.5–62.5° C.) were obtained.

Example 2

LDEE Acetate 10.0 g dry LDEE were suspended in 50 ml absolute alcohol and 2.666 g glacial Acetic acid (1 equivalent) were added with stirring at ambient temperature. After complete dissolution of the solids, the clear solution was transferred to a round-bottom flask and the solvent was evaporated in Rotavapor under vacuum. The evaporation flask was heated in a water bath (50° C.). After the solvent evaporation, 100 ml Toluene were introduced and evaporated under the same conditions. After the Toluene evaporation, another portion of 100 ml Toluene was introduced and evaporated under the same conditions. The evaporation residue was dried in a vacuum oven at 40° C. Then, the semi-solid product was cooled in a freezer, solidified and ground in a mortar. The ground solid product was dried at room temperature in a vacuum oven. The resulting powder has melting range of 42.5–46.5° C. The hygroscopicity test at RH=80% and T=20±2° C. showed a weight gain of 6.7% during 24 hrs.

Example 3

LDEE Mesylate 10.0 g dry LDEE were suspended in 50 ml absolute alcohol and 4.267 g Methanesulfonic acid (1 equivalent) were added with stirring at ambient temperature. After complete dissolution of solids, the clear solution was transferred to a round-bottom flask and the solvent was evaporated in Rotavapor under vacuum. The evaporation flask was heated in a water bath (50° C.). After the solvent evaporation, 100 ml Toluene were introduced and evaporated under the same conditions. After the Toluene evaporation, another portion of 100 ml Toluene was introduced and evaporated under the same conditions. The evaporation residue was dried in a vacuum oven at 40° C. Then, the semi-solid product was cooled in a freezer, solidified and ground in a mortar. The ground product has a melting point of 53.5° C. The hygroscopicity test at RH=80% and T=20±2° C. showed a weight gain of 17.5% during 24 hrs.

Example 4

LDEE L(+)Tartrate 10.0 g dry LDEE were suspended in 50 ml absolute alcohol and 6.665 g L(+)Tartaric acid dry powder (1 equivalent) were added. The suspension was stirred and heated, and at 41° C., complete dissolution of the solids was observed. The solution was cooled without precipitation to 8° C. and at 8–10° C., 50 ml Toluene were added dropwise with stirring. White semi-solid product was precipitated. The precipitate was separated from the solution by decantation, dried at 40° C. in a vacuum oven and ground. The resulting solid product has a melting range of 79–86° C. The hygroscopicity test at RH=80% and T=20±2° C. showed a weight gain of 7.1% during 24 hrs.

Example 5

LDEE Hydrogen L(+)Tartrate 10.0 g dry LDEE were suspended in 35 ml absolute alcohol and 3.332 g L(+)Tartaric acid dry powder (0.5 equivalent) were added with stirring. The suspension was heated and stirred, and at 50° C. after complete dissolution of the solids, the solution was transferred to a round-bottom flask. Then, the solvent was evaporated on Rotavapor under vacuum. The evaporation flask was heated in a water bath (50° C.). 50 ml Toluene was introduced into evaporation residue and evaporated under the same conditions. After the evaporation, another 30 ml Toluene was added and evaporated under the same conditions. The solid evaporation residue, a white powder, was dried in a vacuum oven at room temperature. The melting range is 71.5–73.0° C. The hygroscopicity test at RH=80% and T=20±2° C. showed a weight gain of 10.1% during 24 hrs.

Example 6

LDEE D(−)Tartrate 10.0 g dry LDEE were suspended in 50 ml absolute ethanol and 6.665 g D(−)Tartaric acid dry powder (1 equivalent) were added with stirring. Then, the suspension was heated and after dissolution of the solids at 50° C., the solution was transferred to a round-bottom flask. Then, the solvent was evaporated on Rotavapor under vacuum. The evaporation flask was heated in a water bath (50° C.). After the evaporation, 60 ml Toluene were introduced into the residue and evaporated under the same conditions. After the Toluene evaporation, another 60 ml Toluene were introduced and evaporated under the same conditions. The solid residue was ground and the resulting powder dried in a vacuum oven at 40° C. The melting range is 74–77° C. The hygroscopicity test at RH=80% and T=20±2° C. showed a weight gain of 6.7% during 24 hrs.

Example 7

LDEE (LD)Tartrate 10.0 g dry LDEE were suspended in 50 ml absolute alcohol and 6.664 g (LD)Tartaric acid dry powder (1 equivalent) were added with stirring. The suspension was heated and after dissolution of solids at 53° C., the solution was transferred to a round-bottom flask. The solvent was evaporated on Rotavapor under vacuum and the evaporation flask was heated in a water bath (50° C.). After the solvent evaporation, 60 ml Toluene were introduced to the residue and evaporated under the same conditions. After the Toluene evaporation, another 60 ml Toluene was introduced and evaporated under the same conditions. The resulting solid product was ground and dried in a vacuum oven at 40° C. The melting range is 71.7–76.8° C. The hygroscopicity test at RH=80% and T=20±2° C. showed a weight gain of 6.3% during 24 hrs.

Example 8

LDEE Benzoate 10.0 g dry LDEE were suspended in 50 ml absolute alcohol and 5.423 g dry Benzoic acid (1 equivalent) were added with stirring. After complete dissolution of solids at ambient temperature, the solution was transferred to a round-bottom flask. The solvent was evaporated in Rotavapor under vacuum and the evaporation flask was heated in a water bath (50° C.). After the solvent evaporation, 50 ml Toluene were introduced to the residue and evaporated under the same conditions. After the Toluene evaporation, another 50 ml Toluene were introduced and evaporated under the same conditions. After the Toluene evaporation, 50 ml Ethylacetate were introduced into the residue and evaporated under the same conditions. The resulting solid product was cooled in a freezer and after solidification, ground and dried in a vacuum oven at room temperature. The melting range is 54.3–57° C. The hygroscopicity test at RH=80% and T=20±2° C. showed a weight gain 4.1% during 24 hrs.

Example 9

LDEE Benzoate Precipitation 10 g semi-solid LDEE Benzoate were dissolved in 50 ml chloroform with heating. Then, about 80% of the solvent was evaporated in Rotavapor under vacuum at ambient temperature. The residue was stirred and 50 ml Hexane were added at room temperature. White solids were precipitated and the suspension was stirred and filtrated. The solid product was dried under vacuum and ground. The melting range is 55.3–58.1° C.

Example 10

LDEE Phenylbutyrate 10.0 g dry LDEE were suspended in 50 ml absolute alcohol and 7.291 g of dry Phenylbutyric acid (1 equivalent) were added. The resulting suspension was stirred and heated, after dissolution of the solids at 43° C., the solution was transferred to a round-bottom flask. The solvent was evaporated in Rotavapor under vacuum and the evaporation flask was heated in a water bath (50° C.). After the solvent evaporation, 60 ml Toluene were introduced to the residue and evaporated under the same conditions. After the Toluene evaporation, another 60 ml Toluene were introduced and evaporated under the same conditions. The resulting liquid residue was dissolved in 100 ml chloroform and 75% of the solvent was evaporated in Rotavapor under vacuum. During the chloroform evaporation, solid product was precipitated, the suspension was filtered and solids were dried in a vacuum oven at 40° C. The solid product was re-precipitated from 5 volumes of chloroform and dried under vacuum at room temperature. The melting range is 31.1–33.5° C. The hygroscopicity test at RH=80% and T=20±2° showed a weight gain of 1.03% during 24 hrs.

Example 11

LDEE Phosphate 10.0 g dry LDEE were suspended in 50 ml absolute alcohol and a solution of 2.90 g anhydrous Phosphoric acid in 50 ml absolute alcohol (0.333 equivalent) was added. Then, the mixture was stirred and heated. After complete dissolution of the solids at 39° C., the solvent was evaporated in Rotavapor under vacuum and the evaporation flask was heated in a water bath (50° C.). After the solvent evaporation, 50 ml Ethylacetate were introduced to the residue and evaporated under the same conditions. After the Ethylacetate evaporation, 50 ml Toluene were introduced and evaporated under the same conditions. After the Toluene evaporation, another 50 ml Toluene were introduced and evaporated under the same conditions. The solid residue was dried in a vacuum oven at 40° C. and ground. The melting range is 74–85.5° C. The hygroscopicity test at RH=80% and T=20±2° C. showed a weight gain of 6.4% during 24 hrs.

Example 12

LDEE Citrate 10.0 g dry LDEE were suspended in 50 ml absolute alcohol. 2.844 g of Citric acid (0.333 equivalent) powder were added and then heated to dissolution. The solution was transferred to a round-bottom flask. Then, the solvent was evaporated in Rotavapor under vacuum and the evaporation flask was heated in a water bath (50° C.). After the solvent evaporation, 60 ml Toluene were introduced to the residue and evaporated under the same conditions. After the Toluene evaporation, another 60 ml Toluene were introduced and evaporated under the same conditions. The resulting residue of evaporation is a white, flowable powder with a melting range of 62.6–67.8° C. The hygroscopicity test at RH=80% and T=20±2° C. showed a weight gain of 6.3% during 24 hrs.

Example 13

LDEE Citrate Precipitation

Solid Citrate from Example 11 was dissolved by being heated in a mixture of IPA:Ethylacetate (1:3, 10 volumes). The solution was cooled and the solid precipitate was filtered and dried under vacuum at room temperature. The resulting snow-white powder has a melting range of 73.6–82.5° C.

Example 14

LDEE Ascorbate 10.0 g dry LDEE were suspended in 50 ml absolute alcohol and 7.821 g Ascorbic acid (1 equivalent) powder were added with stirring. The suspension was stirred and heated and at 73° C., complete dissolution of solids was observed. The solution was transferred to a round-bottom flask. The solvent was evaporated in Rotavapor under vacuum and the evaporation flask was heated in a water bath (50° C.). After the solvent evaporation, 50 ml Toluene were introduced to the residue and evaporated under the same conditions. After the Toluene evaporation, another 50 ml Toluene were introduced and evaporated under the same conditions. The resulting residue was dried in a vacuum oven at 40° C. The dry product, a pink powder, has a melting range of 73.7–75.8° C. The hygroscopicity test at RH=80% and T=20±2° C. showed a weight gain of 7.04% during 24 hrs.

Example 15

LDEE S(+)Mandelate 10.0 g dry LDEE were suspended in 50 ml of absolute alcohol. 6.754 g S(+)Mandelic acid (1 equivalent) powder were added with stirring and heated for complete dissolution. The solution was transferred to a round-bottom flask. The solvent was evaporated in Rotavapor under vacuum and the evaporation flask was heated in a water bath (50° C.). After the solvent evaporation, 50 ml Toluene were introduced to the residue and evaporated under the same conditions. After the Toluene evaporation, another 50 ml Toluene were introduced and evaporated under the same conditions. The resulting solid residue was ground and dried in a vacuum oven at 40° C. The dry product has a melting range of 56.2–59.1° C. The hygroscopicity test at RH=80% and T=20±2° C. showed a weight gain of 4.02% during 24 hrs.

Example 16

LDEE S(+)Mandelate Precipitation

The solid product from the Example 14 was dissolved in 20 volumes of chloroform with heating, then the solvent was evaporated in Rotavapor under vacuum. White solid product was precipitated during the evaporation. The solid product was dried under vacuum at room temperature and ground. The melting range is 69.9–77.2° C.

Example 17

LDEE R(−)Mandelate 10.0 g dry LDEE were suspended in 50 ml of absolute alcohol. 6.754 g R(−) Mandelic acid (1 equivalent) powder were added with stirring and heated for complete dissolution. The solution was transferred to a round-bottom flask. The solvent was evaporated in Rotavapor under vacuum and the evaporation flask was heated in a water bath (50° C.). After the solvent evaporation, 60 ml Toluene were introduced to the residue and evaporated under the same conditions. After the Toluene evaporation, another 60 ml Toluene were introduced and evaporated under the same conditions. The resulting solid residue was ground and dried in a vacuum oven at 40° C. The dry product has a melting range of 62.2–67.2° C. The hygroscopicity test at RH=80% and T=20±2° C. showed a weight gain of 5.4% during 24 hrs.

Example 18

LDEE Valerate 10.0 g dry LDEE were suspended in 50 ml of absolute alcohol. 4.534 g Valeric acid (1 equivalent) were added with mixing and the mixture was heated. After complete dissolution of the solids at 40° C., the solution was transferred to a round-bottom flask. The solvent was evaporated in Rotavapor under vacuum, and the evaporation flask was heated in a water bath (40° C.). After the solvent evaporation, 50 ml Toluene were introduced to the residue and evaporated under the same conditions. After the Toluene evaporation, the residue was dissolved in 50 ml of Chloroform and the solvent was evaporated under the same conditions. The procedure of Chloroform addition and evaporation was repeated 3 times under the same conditions. The resulting semi-solid residue was dried under vacuum at room temperature. A colorless liquid with a melting point below 20° C. was obtained.

Example 19

LDEE Octanoate 10.0 g dry LDEE were suspended in 50 ml of absolute alcohol. 6.403 g of Octanoic acid (1 equivalent) were added and after complete dissolution of the solids, the solution was transferred to a round-bottom flask. The solvent was evaporated in Rotavapor under vacuum and the evaporation flask was heated in a water bath (50° C.). After the solvent evaporation, 50 ml Toluene were introduced to the residue and evaporated under the same conditions. After the Toluene evaporation, the residue was dissolved in 50 ml Chloroform and the solvent was evaporated under vacuum at room temperature. The procedure of Chloroform addition and evaporation was repeated twice under the same conditions. The solid residue obtained by evaporation was dried under vacuum at room temperature and ground in a mortar. The resulting white, flowable powder has a melting range of 70.8–72.9° C. The hygroscopicity test at RH=80% and T=20±2° C. showed a weight gain of 0.22% during 24 hrs.

Example 20

LDEE Palmitate 10.0 g dry LDEE were suspended in 50 ml of absolute alcohol. 5.69 g Palmitic acid (1 equivalent) powder were added with stirring. The suspension was stirred and heated and at 29° C., complete dissolution of the solids was observed. The solution was transferred to a round-bottom flask. The solvent was evaporated in Rotavapor under vacuum and the evaporation flask was heated in a water bath (50° C.). After the solvent evaporation, 50 ml Chloroform were introduced to the residue and evaporated under the same conditions. After the Chloroform evaporation, 50 ml Toluene were introduced and evaporated under the same conditions. After the Toluene evaporation, the residue was dissolved in 50 ml Chloroform and the solvent was evaporated under vacuum at room temperature in Rotavapor. The Chloroform introduction and evaporation procedure was repeated twice under the same conditions. The residue was dried under vacuum at room temperature. The resulting yellowish-white, semi-solid product has a melting point below 20° C.

Example 21

LDEE Adipate Ethanolate 10.0 g dry LDEE were suspended in 50 ml absolute alcohol. 3.244 g Adipic acid (0.5 equivalent) dry powder were added with stirring. The mixture was heated and after dissolution of the solids at 26° C., the solution was transferred to a round-bottom flask. The solvent was evaporated in Rotavapor under vacuum and the evaporation flask was heated in a water bath (45° C.). After the solvent evaporation, 60 ml Toluene were introduced to the residue and evaporated under the same conditions. The solid evaporation residue was dried under vacuum at room temperature and ground in a mortar. The resulting white powder has a melting range of 46.5–51.6° C. The hygroscopicity test at RH=80% and T=20±2° C. showed a weight gain of 5.25% during 24 hrs.

Example 22

LDEE Succinate Ethanolate 10.0 g dry LDEE were suspended in 50 ml absolute alcohol. 2.622 g Succinic acid (0.5 equivalent) dry powder were added and the mixture was stirred until complete dissolution of the solids at 25° C. Then, the solution was transferred to a round-bottom flask. The solvent was evaporated in Rotavapor under vacuum and the evaporation flask was heated in a water bath (40° C.). The solid evaporation residue was dried under vacuum at room temperature and ground in a mortar. The resulting white powder has a melting range of 60–61.3° C. The hygroscopicity test at RH=80% and T=20±2° C. showed a weight gain of 4.3% during 8 hrs.

Example 23

LDEE Succinate Dihydrate 10.0 g dry LDEE were suspended in 50 ml absolute alcohol. 2.622 g Succinic acid (0.5 equivalent) dry powder were introduced and 30 ml of water were added to the mixture with stirring. After complete dissolution of the solids, the solution was transferred to a round-bottom flask. The solvent was evaporated in Rotavapor under vacuum and the evaporation flask was heated in a water bath (40° C.). After the solvent evaporation, 80 ml Toluene were introduced to the residue and evaporated under the same conditions. The solid evaporation residue was dried under vacuum at room temperature and ground in a mortar. The resulting white flowable powder has a melting range of 93.4–95.9° C. The hygroscopicity test at RH=80% and T=20±2° C. showed a weight gain of 0.27% during 24 hrs.

Example 24

Crystallized LDEE Succinate Dihydrate 10.0 g dry LDEE were suspended in 50 ml 95% alcohol. A solution of 2.622 g of Succinic acid in 40 ml 95% alcohol was prepared and heated to 33° C. for complete dissolution. The Succinic acid solution was mixed with the LDEE suspension. After complete dissolution of the solids, the mixture was seeded with solid LDEE Succinate Hydrate.

White crystalline solids were precipitated at room temperature during 12 hrs. The suspension was filtered and solids were washed on a filter with absolute alcohol. The product was dried under vacuum at room temperature, yielding 10.6 g. The product has a melting range 96.1–97.6° C.

Example 25

Crystallized LDEE Fumarate Dihydrate 20.0 g of dry LDEE were suspended in 120 ml 95% alcohol. 5.15 g of Fumaric acid were suspended in 50 ml 95% alcohol. The Fumaric acid suspension was introduced into the LDEE suspension with stirring; after complete dissolution of the solids, a small sample of the solution was evaporated to dryness. The solution was seeded with stirring with resulting crystalline material. After the seeding, crystallization was developed at 20–22° C., the batch was cooled to 12° C., solid product was filtered and washed with 95% alcohol. The product was dried under vacuum at 50° C., yielded 23.7 g, and the resulting product was white flowable powder with a melting range of 100.6–109.4° C. The hygroscopicity was tested at RH=80% and T=20±2° C. The weight gain was 0.04% during 24 hrs.

Example 26

LDEE Oleate 3.9 g of dry LDEE were suspended in 30 ml absolute alcohol. The suspension was stirred and after dissolution of solids, 4.9 g of Oleic acid (1 equivalent) was introduced with stirring. The resulting solution was transferred to a round-bottom flask. The solvent was evaporated in Rotavapor under vacuum, and the evaporation flask was heated in a water bath (50° C.). After the solvent evaporation, the residue was dissolved in 40 ml of chloroform and the solvent was evaporated under the same conditions. The liquid evaporation residue was dissolved in chloroform and solvent evaporation was repeated under the same conditions. The resulting residue was a liquid with a melting point below 20° C.

Example 27

LDEE Myristate 10.0 g of dry LDEE were suspended in 50 ml of absolute alcohol. The suspension was stirred and 10.142 g of Myristic acid powder (1 equivalent) were added. The mixture was stirred and heated; after complete dissolution of solids at 25° C., the solution was transferred to a round-bottom flask and the solvent was evaporated in Rotavapor under vacuum, and the evaporation flask was heated in a water bath (50° C.). After the solvent evaporation, 50 ml of chloroform were introduced into the residue and evaporated under the same conditions. The procedure of chloroform addition and evaporation was repeated 3 times. The resulting evaporation residue was dried under vacuum at room temperature. The solid product was ground in a mortar and dried under the same conditions for an additional 12 hrs. The dry product (white flowable powder) had a melting range of 46–48.7° C. The hygroscopicity was tested at RH=80% and T=20±2° C. and the weight gain was 0.11% during 24 hrs.

Example 28

LDEE Maleate Ethanolate 20.0 g of dry LDEE were suspended in 140 ml 95% alcohol. 5.15 g of Maleic acid powder (1 equivalent) were introduced into the suspension at ambient temperature with stirring. Complete dissolution of solids was observed and the resulting solution was sampled. The sample was evaporated to dryness and the dry solid (white powder) was used for seeding of the solution at 28° C. After the seeding, the solution was stirred and no crystallization was observed. Seeding solids were dissolved in a seconds. The seeding was repeated twice and no crystallization was observed. The solution was transferred to a round-bottom flask and the solvent was evaporated in Rotavapor under vacuum, and the evaporation flask was heated in a water bath (50° C.). After the solvent evaporation, 80 ml of toluene were introduced into the residue and evaporated under the same conditions. The residue of toluene evaporation was mixed with 60 ml of chloroform and evaporated under the same conditions. The resulting evaporation residue was dried under vacuum at room temperature. The solid product was ground in mortar and dried under vacuum at ambient temperature. The dry product (white powder) had a melting range of 55–57.3° C. Hygroscopicity was tested at RH=80% and T=20±2° C. and weight gain was 3.1% during 24 hrs.

Example 29

Stability of Dihydrates

The stability of succinate dihydrate and fumarate dihydrate were investigated under the following test conditions: 8 days at 65° C. in glass vial (air) (Table 1).

TABLE 1

Stability of crystalline hydrates of LDEE

| Impurity Profile (HPLC) | Succinate dihydrate Start | End | Fumarate dihydrate Start | End |
|---|---|---|---|---|
| Assay LDEE (%) | 74.1 | 73.46 | 75.0 | 75.0 |
| L-DOPA (%) | 0.1 | 0.56 | 0.11 | 0.27 |
| LD-LDEE (%) | N.D. | N.D. | L.T. 0.03 | 0.03 |
| cyc.L-DOPA (%) | N.D. | 0.03 | N.D. | L.T. 0.03 |
| Unknown RRT = 0.72 (%) | N.D. | N.D. | N.D. | 0.09 |
| Unknown RRT = 0.83 (%) | N.D. | 0.03 | N.D. | N.D. |

Discussion

Wide screening of LDEE salts formed by organic and inorganic acids was performed. The types of acids and acidic salts are summarized in Tables 2–3. There is no evidence that the type of acid affects the salt properties.

TABLE 2

Type of acids used for preparation of LDEE salts

| Type of acid | Acid | Example No. |
|---|---|---|
| Inorganic oxygen-containing | Phosphoric | 11 |
| Alkyl carboxylic | Acetic | 2 |
|  | Valeric | 18 |
|  | Octanoic | 19 |
|  | Myristic | 27 |
|  | Oleic | 26 |
|  | Palmitic | 20 |
| Aromatic | Benzoic | 8 |
|  | Phenylbutyric | 10 |
| Dicarboxylic | Succinic | 22, 23 |
|  | Fumaric | 25 |
|  | Adipic | 21 |
|  | Maleic | 28 |
| A-Hydroxy carboxylic, -di- and -tricarboxylic | L,D,LD-Tartaric | 4,5,6,7 |
|  | (R), (S) -Mandelic | 15,17 |
|  | Citric | 12 |
| Non-carboxylic | Ascorbic | 14 |
| Sulfonic | Methanesulfonic | 3 |

TABLE 3

Acids and Acidic Salts used for LDEE Salt Preparation

| Acid or Acid Salt | Purity (%) | Source | Properties | $pK_a$ |
|---|---|---|---|---|
| Acetic acid | 99.7+ | Frutarom | Glacial | 4.76 |
| Adipic acid | 99+ | Aldrich | m.p. 152–154° C. | 4.43;5.41 |
| L-Ascorbic acid | 99+ | Sigma | m.p. 193° C. (decomp.) | 4.10 |
| Benzoic acid | 99.9+ | Merck | m.p. 121–123° C. | 4.21 |
| Citric acid | 99.5+ | Fluka | m.p. 152–154° C. | 3.13;4.76;6.40 |
| Fumaric acid | 99+ | Teva | m.p. 299° C. | 3.03;4.54 |
| Maleic acid | 99+ | Acros | m.p. 136–138° C. | 1.92;6.22 |
| S(+)Mandelic acid | 99+ | Janssen | $[a]_D^{20}$+154.8,m.p. 132.6° C. | 3.85 |
| R(−)Mandelic acid | 99+ | Janssen | $[a]_D^{20}$−150° C.,m.p. 130–132° C. | 3.83 |
| Methanesulfonic acid[a] | 99+ | Teva | m.p. 20° C. | 1.2 |
| Myristic acid | 99.5+ | Aldrich | m.p. 55.1° C. | ~4.8 |
| Octanoic acid | 99.5+ | Aldrich | m.p. 16.0–16.5° C. | 4.89 |
| Oleic acid | 99+ | Aldrich | m.p. 6–9° C. | ~4.8 |
| Palmitic acid | 99+ | Aldrich | m.p. 61–64° C. | ~4.8 |
| Phenyl Butyric acid | 98+ | Merck | m.p. 48–51° C. | 4.76 |
| Phosphoric acid[a] | 98+ | Aldrich | Crystalline, very hygroscopic | 2.15;7.20;11.9 |
| Potassium dihydrogen phosphate | 99.5+ | Merck | m.p. 252–254° C. | 3.1 |
| Sodium hydrogen L-Tartrate | 98+ | Aldrich | $[a]_D^{20}$−150°+24° C.,m.p. 253° C. | No data |
| Sodium dihydrogen citrate | 99 | Aldrich | m.p. 212° C. | No data |
| Stearic acid | 98+ | Aldrich | m.p. 67–69° C. | ~4.8 |
| Succinic acid | 99.5+ | Merck | m.p 184–185° C. | 4.16;5.61 |
| L-Tartaric acid | 99.8 | Pahi.S | $[a]_D^{20}$+12.8° C.,m.p. ~170° C. | 2.98;4.34 |
| D-Tartaric acid | 99 | Aldrich | $[a]_D^{20}$−12° C.,m.p. 172–174° C. | 2.98;4.34 |
| Valeric acid | 99+ | Aldrich | m.p. −20—−18° C. | 4.84 |

[a]Hygroscopic acids

Properties of Salts

A detailed analysis of the properties of the salts of the subject invention is presented in Table 4 below.

TABLE 4

| Product (salt) | delta pK$_a$ pK$_a^{LDEE}$ −pK$_a^{acid}$ | Physical form | Appearance | Melting range, °C | pH of water solution | Weight gain during 24 hrs at RH = 80%, % | Mean water absorption rate at RH = 80% mole/kg/hr | Material appearance after 24 hrs at RH = 80% | Color stability at RH = 80%, hrs |
|---|---|---|---|---|---|---|---|---|---|
| LDEE | 0 | Crystalline free base | White powder | 87.1–87.5 | 8.2 | 0.24 | 0.005 | White flowable powder | ~50 |
| Acetate | 2.48 | Amorphous salt | White powder | 42.5–46.5 | | 6.7 | 0.155 | Semi-solid melt | 1.5 |
| Mesylate | 6.04 | Amorphous salt | White powder | 53.5 | | 17.5 | 0.405 | Syrup | >24 |
| Phosphate | 5.09;0.04;−4.6 | Amorphous salt | White powder | 74–86 (dec.99–100) | | 6.4 | 0.147 | Semi-solid melt | 15 |
| Monopotassium phosphate | 4.14 | Mixture | White powder | 83–85 (dec.136–148) | 7.5–8.0 | 1.6 | 0.037 | White flowable powder | >48 |
| Citrate solid | 4.11;4.28;0.84 | Amorphous salt | White powder | 63–67 (dec.90–91) | | 6.3 | 0.146 | Semi-solid melt | 20 |
| Citrate crystallized | 4.11;4.28;0.84 | Amorphous salt | White powder | 79–83 (dec.102–108) | | | | No data | |
| L(+)Tartrate | 4.26;2.90 | Amorphous salt | White powder | 79–86 | | 7.1 | 0.164 | Syrup | 15 |
| Monohydro L (+)Tartrate | 4.26;2.90 | Amorphous salt | White powder | 71.5–73 | | 10.1 | 0.23 | Syrup | 19 |
| D(−)Tartrate | 4.26;2.90 | Amorphous salt[a] | White powder | 74–77 (dec.96–97) | | 6.7 | 0.155 | Syrup | 20 |
| LD Tartrate | 4.26;2.90 | Amorphous salt[a] | White powder | 72–77 (dec.93–94) | | 6.3 | 0.146 | Syrup | 20 |
| R(−)Mandelate from toluene | 3.4 | Amorphous salt[a] | White powder | 62–67 | | 5.4 | 0.125 | Semi-solid melt | >24 |
| R(−)Mandelate from chloroform | 3.4 | Amorphous salt[a] | White powder | 58–62.6 | | 5.4 | 0.125 | Semi-solid melt | >24 |
| S(+)Mandelate solid | 3.4 | Amorphous salt | White powder | 56–59 (dec.99–100) | | 4.0 | 0.092 | Semi-solid melt | >24 |
| S(+)Mandelate from chloroform | 3.4 | Amorphous salt | White powder | 70–77 | | | | No data | |
| Ascorbate | 3.14 | Amorphous salt | Red powder | 73.5–76.0 (dec.91) | 5.5–6.0 | 7.0 | 0.162 | Red semi-solid melt | 0–5 |
| Benzoate solid | 3.03 | Amorphous salt | White powder | 54.3–57.0 | 6 | 4.1 | 0.09 | Semi-solid melt | 4.5 |
| Benzoate crystallized | 3.03 | Amorphous salt | White powder | 55–58 | | | | No data | |
| Phenyl butyrate | 2.48 | Amorphous salt | White powder | 31.1–33.5 | | 1.0 | 0.023 | Semi-solid melt | 1.0 |
| Succinate ethanolate | 3.08; 1.63 | Amorphous salt | White powder | 60–61.5 | | 2.9 | 0.067 | Semi-solid melt | >24 |

TABLE 4-continued

Properties of LDEE salts

| Product (salt) | delta pK$_a$ pK$_a^{LDEE}$ −pK$_a^{acid}$ | Physical form | Appearance | Melting range, °C. | pH of water solution | Weight gain during 24 hrs at RH = 80%,% | Mean water absorption rate at RH = 80% mole/kg/hr | Material appearance after 24 hrs at RH = 80% | Color stability at RH = 80%, hrs |
|---|---|---|---|---|---|---|---|---|---|
| Succinate hydrate | 3.08; 1.63 | Crystalline salt[a] | White powder | 96.1–97.6 | 5.8 | 0.27 | 0.006 | White flowable powder | >72 |
| Adipate ethanolate | 2.81; 1.83 | Amorphous salt | White powder | 47.5–51.5 | 6 | 5.25 | 0.121 | Semi-solid melt | >24 |
| Valerate | ~2.4 | Liquid salt | Yellowish syrup | L.T.20 | | | | No data | |
| Octanoate Palmitate | 2.35 ~2.4 | Crystalline salt[a] Liquid salt | White powder Semi-sold mass | 71–72.5 L.T.20 | 6.0–6.5 | 0.22 | 0.005 | White flowable powder No data | >48 |
| Stearate Oleate | ~2.4 ~2.4 | Mixture Liquid salt | White powder Colorless syrup | 48.5–50 L.T.20 | | 0.03 | 0.0003 | White lump powder | >48 |
| Myristate Fumarate hydrate | ~2.4 4.21; 2.7 | Crystalline salt[a] Crystalline salt[a] | White powder White powder | 45–48.5 100–109 | 5.5 | 0.11 0.04 | 0.002 0.0004 | White flowable powder White flowable powder | >48 >48 |
| Maleate | 5.35; 1.02 | Amorphous salt | White powder | 55.5–57.3 | 6.4 | 3.1 | 0.07 | Yellowish syrup | 3 |

[a]Crystalline non-hygroscopic salts

Hygroscopic Salts

Most of the prepared salts are hygroscopic materials. LDEE as free base is not a hygroscopic material and acids that were used for salts preparation are also not hygroscopic (except phosphoric acid). So for Acetate (Example 2), Mesylate (Example 3), L(+)Tartrate and Hydrogen Tartrate (Examples 4–5), D(−) and (LD)Tartrates (Examples 6–7), Benzoate (Example 8), Phenylbutyrate (Example 10), Citrate (Example 12), Ascorbate (Example 14), S(+) and R(−) Mandelates (Examples 15 and 17), Adipate Ethanolate (Example 21) and Succinate Ethanolate (Example 22), and Maleate Ethanolate (Example 28) solid hygroscopic products are new chemical entities, because a mechanical mixture of two non-hygroscopic and non-reacting products is not hygroscopic.

All of the prepared hygroscopic salts are amorphous (amorphous salts tend to be more hygroscopic than crystalline forms of the same material).

In comparison to crystalline forms, amorphous forms have a wide melting range due to fast water absorption by dry solid from atmospheric air. Amorphous forms also have lower melting points and higher dissolution rates than crystalline forms. In comparison to crystalline forms, amorphous forms are also usually less chemically and physically stable and more hygroscopic. Furthermore, amorphous materials are often more soluble in water than crystalline forms.

It was found that for Citrate, Phosphate, S(+)Mandelate and L(−)Tartrate, exposure to atmospheric air for 30–90 min was enough for significant reduction (10–15° C.) of the melting temperature. Acetate and Mesylate were more sensitive to atmospheric air, both of the salts were deliquescent and transformed into liquid during 3–5 minutes.

Non-Hygroscopic Salts

Four crystalline solid salts of LDEE were found to be non-hygroscopic: LDEE Octanoate (Example 19) and LDEE Succinate Dihydrate (Examples 23 and 24), LDEE Fumarate Dihydrate (Example 25) and LDEE Myristate (Example 27).

Octanoate salt did not absorb water at RH=80%, and after about 48 hrs of exposure in a humidity chamber, it appeared as a white flowable powder. This salt was prepared by solvent evaporation from the reaction mixture as all other salts were prepared (Example 19).

Succinate Dihydrate salt was the second non-hygroscopic crystalline salt. It did not absorb water at RH=80%, and after about 72 hrs of exposure in a humidity chamber, it appeared as a white flowable powder. This material could be prepared by two methods: solvent evaporation from the reaction mixture as all other salts were prepared (Example 23) or by crystallization from 95% alcohol.

Fumarate Dihydrate salt was the third non-hygroscopic crystalline salt. It did not absorb water at RH=80% and after more than 48 hrs of exposure in a humidity chamber, it appeared as white flowable powder. This material was prepared by crystallization from 95% alcohol (Example 25).

Myristate salt was the forth non-hygroscopic crystalline salt. It did not absorb water at RH=80% and after about 24 hrs of exposure in a humidity chamber, it appeared as white flowable powder. This salt was prepared by solvent evaporation from the reaction mixture as all other salts were prepared (Example 27).

Non-hygroscopicity is a major advantage for a drug substance. One of the first goals of chemists in the pharmaceutical industry is to find a non-hygroscopic salt of an active drug. However, non-hygroscopic salts are generally less soluble in water compared to hygroscopic salts, thus the bioavailability of the drug tends to be lower in a non-hygroscopic salt than a hygroscopic salt.

In addition, crystalline drug substances have the following important advantages over amorphous drug substances: higher melting point and narrower melting range, higher density, better processing characteristics of powder (flowable, non-tacky powders), slower dissolution (for slow release drugs), higher chemical and physical stability, and less hygroscopicity.

Non-Solid Salts

Valerate, Palmitate and Oleate (Examples 18, 20, and 26) are non-solid products with melting points below 20° C. As such, the hygroscopicity of these salts is not comparable with solid products.

REFERENCES

1. U.S. Pat. No. 5,607,969, issued Mar. 4, 1997, "L-DOPA ethyl ester to treat Parkinson's disease".
2. U.S. Pat. No. 5,534,885, issued Oct. 11, 1994, "Process for preparing ethyl ester of L-DOPA".
3. U.S. Pat. No. 4,873,263, issued Oct. 10, 1989, "Rectally absorbable form of L-DOPA".
4. British Patent 1,342,286, issued Jan. 3, 1974, "Treatment of Alopecia".
5. "Salt selection, reducing time to market". SSCI Application Notes, No. 4, pp. 1–4, 1999.
6. R. J. Bastin, M. J. Bowker, B. J. Slater, "Salt selection and optimization procedures for pharmaceutical new chemical entities", Organic Process Research and Development, 2000, No. 4, pp. 427–435.
7. K. R. Morris, M. G. Fakes, A. B. Thakur, A. W. Newman, A. K. Singh, J. J. Venit, C. J. Spagnopulo, A. T. Serajuddin, "An integrated approach to the selection of optimal salt form for a new drug candidate" International Journal of Pharmaceutics, 1994, 105, pp. 209–217.
8. K. Marrel, G. Boss, H. van de Waterbeemd, B. Testa, Eur. J. Med. Chem.-Chim. Ther., 1985, 20, No. 5, pp. 459–465.
9. U.S. Pat. No. 6,218,566, issued Apr. 17, 2001.
10. U.S. Pat. No. 5,525,631, issued Jun. 11, 1996.
11. Steng, W., "Physical chemical characterization of drug substances", 1997, DDT 2(10): 415–426.

What is claimed:

1. A non-hygroscopic, crystalline salt of levodopa ethyl ester, wherein the salt is the octanoate salt, the myristate salt, the succinate salt, the succinate dihydrate salt, the fumarate salt or the fumarate dihydrate salt of levodopa ethyl ester.

2. The salt of claim 1, wherein the salt is the octanoate salt of levodopa ethyl ester.

3. The salt of claim 1, wherein the salt is the myristate salt of levodopa ethyl ester.

4. The salt of claim 1, wherein the salt is the succinate salt of levodopa ethyl ester.

5. The salt of claim 1, wherein the salt is the succinate dihydrate salt of levodopa ethyl ester.

6. The salt of claim 1, wherein the salt is the fumarate salt of levodopa ethyl ester.

7. The salt of claim 1, wherein the salt is the fumarate dihydrate salt of levodopa ethyl ester.

8. A composition comprising the salt of levodopa ethyl ester according to claim 1 and a carrier.

9. A pharmaceutical composition comprising an amount of the salt according to claim 1 sufficient to produce a therapeutically effective amount of levodopa and a pharmaceutically acceptable carrier.

10. A method for treating a subject suffering from a disease, wherein the disease is Parkinson's disease, senile dementia, dementia of the Alzheimer's type, a memory disorder, depression, hyperactive syndrome, an affective illness, a neurodegenerative disease, a neurotoxic injury, brain ischemia, a head trauma injury, a spinal trauma injury, schizophrenia, an attention deficit disorder, multiple sclerosis, withdrawal symptoms, epilepsy, convulsions or seizures comprising administering to the subject an amount of the salt according to claim 1 sufficient to produce an amount of levodopa effective to treat the disease.

11. The method according to claim 10, wherein the disease is Parkinson's disease.

12. The method according to claim 10, wherein the amount of the salt of levodopa ethyl ester sufficient to produce an amount of levodopa effective to treat the disease is an amount from 100 mg to 600 mg.

13. The method according to claim 10, wherein the administration is oral, buccal, topical, nasal, subcutaneous, rectal, intravenous, intradermal, or intraperitoneal administration.

14. The method according to claim 13, wherein the administration is oral.

15. The method according to claim 10 wherein the subject is human.

16. A method of providing increased plasma levels of levodopa in a subject in need of increased plasma levels of levodopa comprising administering to the subject the pharmaceutical composition according to claim 9.

17. The method of claim 16, wherein the subject is human.

18. A process for producing a salt of levodopa ethyl ester, which comprises:
  (a) reacting levodopa ethyl ester with an acid, wherein the acid is octanoic acid, myristic acid, succinic acid or fumaric acid, so as to form a salt solution; and
  (b) recovering the salt so formed
thereby producing the salt of levodopa ethyl ester.

19. A process for producing the composition of claim 8 comprising admixing the salt of levodopa ethyl ester, and a carrier.

20. A process for producing the pharmaceutical composition of claim 9 comprising admixing the salt of levodopa ethyl ester, and a pharmaceutically acceptable carrier.

* * * * *